(12) United States Patent
Kwon et al.

(10) Patent No.: US 10,478,440 B2
(45) Date of Patent: Nov. 19, 2019

(54) PHARMACEUTICAL COMPOSITIONS FOR INHIBITING ANGIOGENESIS COMPRISING PLANT-DERIVED NATURAL COMPOUND

(71) Applicant: INDUSTRY-ACADEMIC COOPERATION FOUNDATION, YONSEI UNIVERSITY, Seoul (KR)

(72) Inventors: Ho Jeong Kwon, Seoul (KR); Yong Hyo Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 15/591,709

(22) Filed: May 10, 2017

(65) Prior Publication Data

US 2017/0239266 A1     Aug. 24, 2017

Related U.S. Application Data

(62) Division of application No. 14/361,271, filed as application No. PCT/KR2012/010181 on Nov. 28, 2012, now abandoned.

(30) Foreign Application Priority Data

Nov. 28, 2011 (KR) .................. 10-2011-0124887

(51) Int. Cl.
*A61K 31/55* (2006.01)
*A61P 35/00* (2006.01)
*A61K 31/407* (2006.01)
*A61K 31/5517* (2006.01)

(52) U.S. Cl.
CPC ............ *A61K 31/55* (2013.01); *A61K 31/407* (2013.01); *A61K 31/5517* (2013.01)

(58) Field of Classification Search
CPC ................................ A61K 31/55; A61P 35/00
See application file for complete search history.

(56) References Cited

U.S. PATENT DOCUMENTS

2007/0232588 A1   10/2007   Stella et al. ............. 514/214.03

FOREIGN PATENT DOCUMENTS

WO    WO 99-48501    9/1999  ............. A61K 31/55

OTHER PUBLICATIONS

American Brain Tumor Association (ABTA) http://www.abta.org/brain-tumor-information/types-of-tumors/glioma.html?print=t. Mar. 9, 2016. (Year: 2016).*
David Louis (Annual Review of Pathology: Mechanisms of Disease; vol. 1:pp. 97-117. 2006). (Year: 2006).*
Johnson et al. (Relationships between drug activity and NCI preclinical in vitro and in vivo models and early clinical trials; British Journal of Cancer; (2001) 84 (10), 1424-1431). (Year: 2001).*
Gupta et al., Postgrad. Med. J., vol. 81, pp. 236-242 (2005). (Year: 2005).*
Okuyama et al. (Chem. Pharm. Bull. 40(8):2075-2079. 1992) (Year: 1992).*
Voskoglou-Nomikos et al. (Clinical Predictive Value of the in Vitro Cell Line, Human Xenograft, and Mouse Allograft Preclinical Cancer Models; Clinical Cancer Research; vol. 9: 4227-4239; Sep. 15, 2003). (Year: 2003).*
Ortega et al. (Journal of Clinical Neuroscience; 21 (2014) 1709-1713). (Year: 2014).*
Amiri-Kordestani et al. JNCI J Natl Cancer Inst. vol. 104, Issue 8. (2012): 2 pages. (Year: 2012).*
Pereira, C. G. et al. "Anticancer activity of Tabernaemontana catharinensis extract obtained by supercritical fluid extraction" Rev. Bras. Pl. Med., Botucatu, 2006, vol. 8, No. 4, pp. 144-149. (See abstract, figures 2 and 3).
Jin, Y.-S, et al. "A new indole alkaloid from Ervatamia yurmanensis" Fitoterapia, 2010, vol. 81, pp. 63-65. (See abstract and figure 1).
International Search Report from corresponding PCT Application No. PCT/KR2012/010181, dated Feb. 26, 2013.
Office Action from corresponding U.S. Appl. No. 14/361,271, dated Jul. 28, 2016.
Office Action from corresponding U.S. Appl. No. 14/361,271, dated Feb. 10, 2017.

* cited by examiner

*Primary Examiner* — Rachael E Bredefeld
*Assistant Examiner* — Chris E Simmons
(74) *Attorney, Agent, or Firm* — Harness, Dickey & Pierce, P.L.C.

(57) ABSTRACT

The present invention provides a pharmaceutical composition for inhibiting angiogenesis containing a plant-derived natural compound which can be effective for preventing or treating disorders or diseases associated with angiogenesis. The compound used as an active ingredient in the pharmaceutical composition of the present invention suppresses VEGF-induced angiogenic responses without cytotoxicity at a low concentration by inhibiting the expression of an anti-angiogenic factor (for example, VEGF), and thus remarkably improves the safety of a drug.

3 Claims, 10 Drawing Sheets

PHARMACEUTICAL COMPOSITIONS FOR INHIBITING ANGIOGENESIS COMPRISING PLANT-DERIVED NATURAL COMPOUND

CROSS-REFERENCE TO RELATED APPLICATIONS

This application is a divisional application of U.S. application Ser. No. 14/361,271 filed 28 May 2014, which is a national phase application of PCT Application No. PCT/KR2012/010181 filed 28 Nov. 2012, which claims benefit to Korean Application No. 10-2011-0124887 filed 28 Nov. 2011. The entire disclosure of the applications identified in this paragraph is incorporated herein by references.

TECHNICAL FIELD

The present invention relates to a pharmaceutical composition for inhibiting angiogenesis comprising, as an active ingredient, a plant-derived natural compound having anti-angiogenic activity.

DESCRIPTION OF THE RELATED ART

Angiogenesis, the formation of new blood vessels from existing microvessels, is important in embryogenesis, wound healing, and tissue or organ regeneration [1,2]. However, pathological angiogenesis can lead to solid tumor growth and metastasis, diabetic retinopathy, and other diseases [3,4]. Accordingly, the inhibition of angiogenesis is considered a promising strategy for the treatment of cancer and other human diseases linked with angiogenesis [2,5].

Natural compounds have played a positive role in the advancement of new bioactive small molecules as leads for drug development [6]. Some natural compounds act as anti-viral, anti-bacterial, and anti-cancer agents. For instance, etoposide, a topoisomerase inhibitor derived from podophyllotoxin, a toxin found in the Podophyllum peltatum, prevents the re-ligation of DNA strands. Accordingly, it is used as a chemotherapeutic agent for the treatment of cancers such as Ewing's sarcoma, lung cancer, testicular cancer, lymphoma, non-lymphocytic leukemia, and glioblastoma multiforme [7].

As part of our continuous efforts to discover new anti-angiogenic agents from the natural plants, using cell-based screening, we screened 300 crude extracts of natural plants for their effects on HUVEC proliferation. We discovered that voacangine, a new natural small molecule, possesses anti-angiogenic properties. Voacangine (12-methoxyibogamine-18-carboxylic acid methyl ester), an indole alkaloid, was isolated from root bark of the Voacanga africana and Tabernaemontana catharinensis trees (FIG. 1a). A crude extract of Tabernaemontana catharinensis, which contained voacangine, was reported to be a potent anti-cancer agent [8]. Voacangine has also been shown to inhibit capsaicin contraction in a dose-dependent manner [9]. However, there have been no reports demonstrating the anti-angiogenic activity of the compound. Here, we report for the first time that voacangine is a new natural small molecule that inhibits angiogenesis in vitro and in vivo at a nontoxic dose.

Nicotine as one of main ingredients of tobacco has been reported as a factor for promoting angiogenesis, cancer cell proliferation and progression of arteriosclerosis [16]. As described above, angiogenesis causes growth and metastasis of solid tumors, diabetic retinopathy and some diseases.

Based on properties of voacangine which has been described as active ingredients in anti-angiogenic pharmaceutical compositions comprising plant-derived natural compounds filed in Korean Pat. Appln. No. 10-2011-0124887, the present inventors have analyzed and verified regulation of nicotine-induced angiogenesis as well as potentials as inhibitors to nicotine-induced angiogenesis to suppress nicotine-induced cancer cell proliferation and disease progression due to nicotine poisoning.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THE INVENTION

Technical Problem

The present inventors have endeavored to develop an anti-angiogenic agent for effectively inhibiting angiogenesis without cytotoxicity. As a result, the present inventors have discovered voacangine having anti-angiogenic activity from Voacanga africana, and have found that voacangine may inhibit tumor cell-induced angiogenesis as well as VEGF- or hypoxia-induced angiogenesis, thereby being capable of being applied to prevention or treatment of various angiogenesis-related diseases, disorders, or conditions.

Therefore, the present invention has been made in view of the above-mentioned problems, and an aspect of the present invention is to provide a pharmaceutical composition for inhibiting angiogenesis containing a plant-derived natural compound.

Other purposes and advantages of the present disclosure will become clarified by the following detailed description of invention, claims, and drawings.

Technical Solution

In accordance with an aspect of the present invention, there is provided a pharmaceutical composition for inhibiting angiogenesis, the composition comprising, as an active ingredient, a compound represented by Chemical Formula 1 below:

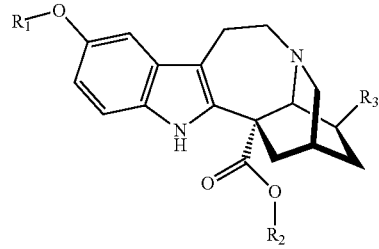

Chemical Formula 1 wherein, $R_1$, $R_2$, and $R_3$ each are independently hydrogen, $C_{1-12}$ alkyl, $C_{1-12}$ alkoxy, hydroxy, CN, $CONH_2$, halo, oxazolyl, $C_{1-12}$ alkylthio, or trifluoro($C_{1-2}$) alkyl.

The present inventors have endeavored to develop an anti-angiogenic agent for effectively inhibiting angiogenesis without cytotoxicity. As a result, the present inventors have discovered voacangine having anti-angiogenic activity from Voacanga africana, and have found that voacangine can inhibit tumor cell-induced angiogenesis as well as VEGF- or hypoxia-induced angiogenesis, thereby being capable of being applied to prevention or treatment of various angiogenesis-related diseases, disorders, or conditions.

The composition of the present invention is expressed as "a pharmaceutical composition for inhibiting angiogenesis", which may be interchangeably expressed as "a pharmaceutical composition for prevention or treatment of angiogenesis-related diseases" or "a pharmaceutical composition for prevention or treatment of uncontrolled angiogenesis-related diseases".

The compound used as an active ingredient in the pharmaceutical composition of the present invention is represented by Chemical Formula 1. In Chemical Formula 1 which defines the compound of the present invention, the term "$C_{1-12}$ alkyl" refers to straight chain or branched chain saturated hydrocarbon group having 1-12 carbon atoms, and preferably $C_1$-$C_4$ straight chain or branched chain alkyl, which is a lower alkyl and includes methyl, ethyl, n-propyl, isopropyl, isobutyl, n-butyl, and t-butyl. The term "alkoxy" refers to —O-alkyl group. When the compound is substituted with a substituted $C_1$-$C_4$ alkyl group, it is substituted with halo-, preferably chloro-, and more preferably fluoro-substituted alkyl group. The term "halo" refers to a halogen group, which includes, for example, fluoro, chloro, bromo, and iodo, and is preferably fluoro, chloro, or bromo atom.

According to a preferable embodiment of the present invention, each $R_1$, $R_2$, and $R_3$ in Chemical Formula 1 is independently hydrogen, halo, or $C_{1-12}$ alkyl.

According to a preferable embodiment of the present invention, the compound of the present invention is represented by Chemical Formula 2 below:

Chemical Formula 2

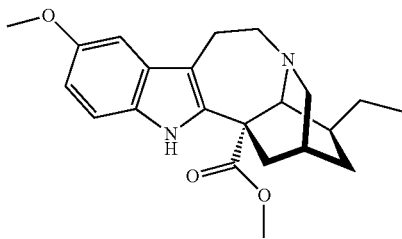

According to a preferable embodiment of the present invention, the compound of the present invention has activity of inhibiting the proliferation of human umbilical vascular endothelial cells (HUVECs). More preferably, the proliferation of the HUVECs is inhibited through the inhibition of expression of hypoxia-inducible factor-1α (HIF-1α) and its target gene, an anti-angiogenic factor (e.g., vascular endothelial growth factor (VEGF)).

According to a preferable embodiment of the present invention, the compound of the present invention has activity of inhibiting tumor cell-induced angiogenesis, that is, hypoxia- or VEGF-induced angiogenesis.

According to a preferable embodiment of the present invention, the compound of the present invention has activity of inhibiting nicotine-induced angiogenesis.

Diseases, disorders or conditions that can be prevented or treated by the pharmaceutical composition of the present invention include various diseases related to angiogenesis. Preferably, the pharmaceutical composition of the present invention is utilized for prevention or treatment of uncontrolled angiogenesis-related diseases or disorders including cancers, diabetic retinopathy, retinopathy of prematurity, corneal graft rejection, neovascular glaucoma, erythema, proliferative retinopathy, psoriasis, hemophiliac joints, capillary proliferation within atherosclerotic plaques, keloids, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation, neurodegenerative diseases, and nicotine addiction-related vessel diseases.

According to a preferable embodiment of the present invention, the cancers capable of being prevented or treated by the composition of the invention include, but are not limited to, brain cancer, neuroendocrine cancer, stomach cancer, lung cancer, breast cancer, ovarian cancer, liver cancer, bronchial cancer, nasopharyngeal cancer, laryngeal cancer, pancreatic cancer, bladder cancer, adrenal cancer, colorectal cancer, colon cancer, cervical cancer, prostate cancer, bone cancer, skin cancer, thyroid cancer, parathyroid cancer, and ureter cancer.

According to a preferable embodiment of the present invention, the autoimmune diseases capable of being prevented or treated by the composition of the present invention include, but are not limited to, alopecia greata, ankylosing spondylitis, antiphospholipid syndrome, autoimmune Addison's disease, autoimmune adrenal disease, autoimmune hemolytic anemia, autoimmune hepatitis, autoimmune ovaritis and testitis, autoimmune thrombocytopenia, Behcet's disease, bullous pemphigoid, cardiomyopathy, celiac sprue-dermatitis, chronic fatigue immune dysfunction syndrome, chronic inflammatory demyelinating polyradiculoneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Grave's disease, Guillain-Barre syndrome, Hashimoto's thyroiditis, idiopathic pulmonary fibrosis, idiopathic thrombocytopenic purpuras, IgA nephropathy, juvenile arthritis, lichen planus, lupus erythematosus, Meniere's disease, mixed connective tissue disease, multiple sclerosis, type I or immune-mediated diabetes, myasthenia gravis, pemphigus vulgaris, pernicious anemia, polyarteritis nodosa, polychondritis, autoimmune polyglandular syndrome, polymyalgia rheumatica, polymyositis and dermatomyositis, primary agammaglobulinemia, primary biliary cirrhosis, psoriasis, psoriatic arthritis, Raynaud's phenomenon, Reiter's syndrome, rheumatoid arthritis, Sarcoidosis, scleroderma, stiff-person syndrome, systemic lupus erythematosus, lupus erythematosus, Takayasu's arteritis, temporal arteritis, giant cell arteritis, ulcerative colitis, uveitis, vitiligo and Wegener's granulomatosis.

According to a preferable embodiment of the present invention, the inflammatory diseases capable of being prevented or treated in the present invention may include: acute or chronic inflammatory disorders, such as inflammatory skin diseases (e.g., asthma, eczema, psoriasis, allergies, rheumatoid arthritis, psoriatic arthritis, atopic dermatitis, psoriasis, acne, atopic rhinitis (hay fever), allergic dermatitis (eczema), chronic sinusitis, or seborrheic dermatitis), bone diseases, gastritis, gout, gouty arthritis, ulcers, chronic bronchitis, acute lung injury, lung inflammation, airway hypersensitivity, inflammatory bowel disease (e.g., Crohn's disease, ulcerative colitis), ankylosing spondylitis, sepsis, septic shock, vasculitis, and bursitis; autoimmune diseases, such as lupus, polymyalgia rheumatic, scleroderma, Wegener's granulomatosis, temporal arteritis, cryoglobulinemia, and multiple sclerosis; transplant rejection; cancers including solid tumors (e.g., lung, CNS, intestine, kidney, and pancreas); Alzheimer's disease; atherosclerosis; viral infections (e.g., HIV or influenza); chronic viral infections (e.g., Epstein-Barr virus, cytomegalovirus, herpes virus; and ataxia telangiectasia.

More preferably, the disease capable of being prevented or treated by the pharmaceutical composition of the present invention is cancers, diabetic retinopathy, or proliferative retinopathy.

According to a preferable embodiment of the present invention, the composition of the present invention includes (a) a pharmaceutically effective amount of the above-described compound of the present invention; and (b) a pharmaceutically acceptable carrier.

As used herein, the term "pharmaceutically effective amount" refers to an amount enough to attain efficacy or activity of the above-described compound or a composition including the compound.

The pharmaceutical composition of the present invention includes a pharmaceutically acceptable carrier. The pharmaceutically acceptable carrier included in the pharmaceutical composition of the present invention is conventionally used in formulations, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include, besides the above components, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

The compound used as an active ingredient in the composition of the present invention may include, besides the compound of Chemical Formula 1 itself, its pharmaceutically acceptable salt, hydrate, or solvate. The term "pharmaceutically acceptable salt" refers to a salt of the compound of Chemical Formula 1, which contains a desired pharmacological effect, that is, activity of inhibiting tumor cell-induced angiogenesis. Examples of this salt are formed by using inorganic acids, such as hydrochloride, hydrobromide, and hydroiodide, and organic acids, such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane propionate, digluconate, dodecylsulfate, ethane sulfonate, fumarate, glucoheptanoate, glycerophosphate, hemisulfate, heptanoate, hexanoate, 2-hydroxyethane sulfate, lactate, maleate, methane sulfonate, 2-naphthalene sulfonate, nicotinate, oxalate, tosylate, and undecanoate.

The term "pharmaceutically acceptable hydrate" refers to a hydrate of the compound of Chemical Formula 1, which has a desired pharmacological effect. The term "pharmaceutically acceptable solvate" refers to a solvate of the compound of Chemical Formula 1, which has a desired pharmacological effect. The hydrate and solvate may be also prepared by using the acids.

The pharmaceutical composition of the present invention may be administered orally or parenterally. Examples of parenteral administration may include intravenous, subcutaneous, intramuscular, intraperitoneal, transdermal injections, mucosal administration, administration of eye drops, and the like.

A suitable dose of the pharmaceutical composition of the present invention may be varied depending on factors, such as formulating method, manner of administration, patient's age, body weight, sex, and morbidity, food, time of administration, route of administration, excretion rate, and response sensitivity. Preferably, the dose of the pharmaceutical composition of the present invention is 0.001-100 mg/kg (body weight) in adults.

The pharmaceutical composition of the present invention may be formulated into a unit dosage form or injected in a multidose container by using a pharmaceutically acceptable carrier and/or excipient, according to the method easily conducted by a person having ordinary skills in the art to which the present invention pertains. Here, the dosage form may be a solution in an oily or aqueous medium, a suspension, a syrup, or an emulsion, an extract, a powder, a granule, a tablet, or a capsule, and may further include a dispersant or a stabilizer.

In accordance with another aspect of the present invention, there is provided a method for inhibiting angiogenesis, the method including administering to a subject the composition of the present invention.

In accordance with still another aspect of the present invention, there is provided a method for preventing or treating cancers, diabetic retinopathy, retinopathy of prematurity, corneal graft rejection, neovascular glaucoma, erythema, proliferative retinopathy, psoriasis, hemophiliac joints, capillary proliferation within atherosclerotic plaques, keloids, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation, neurodegenerative diseases, or nicotine addiction-related vessel diseases, the method including administering a subject the composition of the present invention.

Since the pharmaceutical composition and the compound as an active ingredient of the pharmaceutical composition, which are used in the present invention, are previously described, descriptions thereof are omitted to avoid excessive complication of the specification due to repetitive descriptions thereof.

Advantageous Effects

Features and advantages of the present invention are summarized as follows:

(a) The present invention provides a pharmaceutical composition for inhibiting angiogenesis, capable of being effectively used for prevention or treatment of angiogenesis-related diseases or disorders.

(b) The compound used as an active ingredient in the pharmaceutical composition of the present invention inhibits VEGF-induced angiogenic responses without toxicity in low concentrations by inhibiting expressions of angiogenic factors (e.g., VEGF), and thus significantly improves drug safety.

BRIEF DESCRIPTION OF THE DRAWINGS

FIG. 1a shows the chemical structure of voacangine ($C_{22}H_{28}N_2O_3$, MW 368.4). FIG. 1b shows the effect of crude extract of *Voacanga africana* on the proliferation of HUVECs. FIG. 1c shows the effect of voacangine on cell proliferation. HUVECs were treated with voacangine (1-20 μM) for 3 days, and cell growth was measured using the MTT colorimetric assay. FIG. 1d shows the effect of voacangine on cell viability. Cell viability was examined using the trypan blue assay.

FIG. 2a shows the effect of voacangine on the tube forming ability of HUVECs. Arrows indicates broken tubes formed by VEGF-stimulated HUVECs. FIG. 2b shows inhibitory activity of voacangine on endothelial cell invasion. The basal level capillary tube formation (a) and invasiveness (b) of HUVECs that remained in serum-free media were normalized to 100%.

FIG. 4a shows the expression level of HIF-1α and cyclin D1 were detected by Western blot. The level of tubulin was used as an internal control. FIG. 4b shows the expression level of VEGF protein in HepG2 cells was determined by a VEGF immunoassay. FIG. 4c shows tumor cell-induced angiogenesis. HUVECs were seeded in the upper chamber, and HepG2 was added to the lower chamber without VEGF. Nor, Normoxia; Hyp, Hypoxia.

FIG. 5a shows the effect of voacangine on the tube forming ability of HUVECs. Arrows indicates broken tubes formed by nicotine-stimulated HUVECs. FIG. 5b shows inhibitory activity of voacangine on endothelial cell invasion. The basal level capillary tube formation (a) and invasiveness (b) of HUVECs that remained in serum-free media were normalized to 100%.

PARTICULAR EMBODIMENTS OF THE INVENTION

Figure 1A:
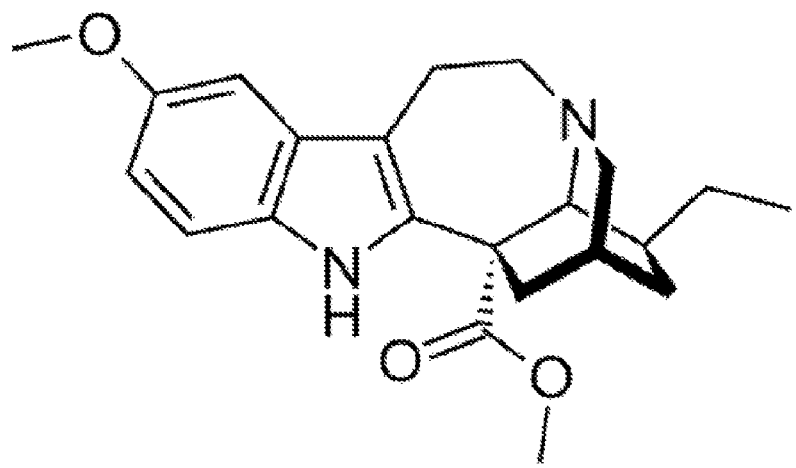
FIGS. 1a-1d represent chemical structure and anti-proliferative activity of voacangine on HUVECs.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods
Materials
Voacangine (12-methoxyibogamine-18-carboxylic acid methyl ester) was purchased from THC Pharm (Frankfurt, Germany). Endothelial growth medium-2 (EGM-2) was purchased from Lonza (Walkersville, Md.). RPMI 1640 and fetal bovine serum (FBS) were purchased from Invitrogen (Grand Island, N.Y.). Vascular endothelial growth factor (VEGF), Matrigel and Transwell chamber systems were obtained from KOMA Biotech (Seoul, Korea), BD Bioscience (Bedford, Mass.) and Corning Costar (Corning, N.Y.), respectively. Anti-HIF-1α, anti-cyclin D1 and anti-tubulin antibody were purchased from BD Bioscience, Cell Signaling (Beverly, Mass.) and Millipore (Billerica, Mass.), respectively.

Cell Culture and Proliferation Assay
Human umbilical vascular endothelial cells (HUVECs) were grown for 7-11 passages in EGM-2 medium supplemented with 10% FBS. HepG2 (human liver carcinoma) cells were grown in RPMI 1640 containing 10% FBS and 1% antibiotics. All cell lines were maintained at 37° C. in a humidified 5% $CO_2$ incubator. Cell proliferation was measured using a 3-(4,5-dimethylthiazol-2-yl)-2,5-diphenyltetrazolium bromide (MTT) colorimetric assay, and cell viability was assessed using Trypan blue staining [10].

Capillary Tube Formation Assay
Matrigel (10 mg/mL) was used to coat a 48-well plate and allowed to polymerize for 1 h at 37° C. HUVECs ($6 \times 10^4$ cells) were seeded on the surface of the Matrigel, and then test compounds were added for 4-16 h at 37° C. in the presence or absence of VEGF (30 ng/mL). Morphological changes in the cells and formation of tubular structures were observed under a microscope (IX71, Olympus) and photographed at 100× magnification (DP70, Olympus) [11].

Chemoinvasion Assay
To examine the invasiveness of HUVECs in vitro, we used a Transwell chamber system with 8.0-μm pore polycarbonate filter inserts [12]. Briefly, the lower side of the filter was coated with gelatin (10 μL, 1 mg/mL) and the upper side was coated with Matrigel (10 μL, 3 mg/mL). Test compounds were added to the lower chamber in the presence of VEGF (30 ng/mL), and HUVECs ($7 \times 10^5$ cells) were placed in the upper chamber of the filter. The chamber was incubated at 37° C. for 18 h, and then the cells were fixed with 70% methanol and stained with hematoxylin and eosin. The invasiveness of cells was measured by counting the number of whole cells in the lower side of the filter using a microscope at 100× magnification, and cells were photographed at 100× magnification.

Chorioallantoic Membrane (CAM) Assay
The CAM assay was performed as described previously [13]. Fertilized chicken eggs were kept in a humidified incubator at 37° C. for 3 days. Approximately 2-3 mL of egg albumin was removed with a hypodermic needle, allowing the CAM and yolk sac to drop away from the shell membrane. On day 5, a 2.5-cm diameter window was made with a razor and tweezers, and a compound-loaded Thermanox coverslip (NUNC, Rochester, N.Y.) was applied to the CAM surface. After further incubation for 2 days, 2-3 mL of Intralipose (Greencross Co, Suwon, Korea) was injected beneath the CAM and the membrane was observed under a microscope. Retinoic acid (RA) was used as a positive control.

Western Blot Analysis and Hypoxic Conditions
The cell lysates were separated by 10% SDS-PAGE, followed by transfer to PVDF membranes (Millipore, Bedford, Mass.) using standard electroblotting procedures. Blots were then blocked and immunolabeled overnight at 4° C. with primary antibodies, including anti-HIF-1α and anti-tubulin antibodies. Immunolabeling was detected by an enhanced chemiluminescence (ECL) kit (GE Healthcare, Buckinghamshire, UK) according to the manufacturer's instructions. For hypoxic conditions, cells were incubated at 5% $CO_2$ with 1% $O_2$ balanced with $N_2$ in an anaerobic chamber (Forma).

Measurement of VEGF by ELISA

The VEGF concentration in media from voacangine-treated cells was determined using a VEGF Immunoassay kit (R&D Systems, Minneapolis, Minn.) according to the manufacturer's instructions. The results were expressed as concentration of VEGF relative to the total amount of VEGF from each well.

In Vitro Tumor Cell-Induced Angiogenesis Assay (Combinated-Chemoinvasion Assay)

To examine the invasive activity of HUVEC-induced tumor cells, a Transwell chamber system with 8.0-μm pore polycarbonate filter inserts was used. Briefly, the lower side of the filter was coated with gelatin (10 μL, 1 mg/mL) and the upper side was coated with Matrigel (10 μL, 3 mg/mL). Next, tumor cell HepG2 was added to the lower chamber. Test compounds were added to the lower chamber without VEGF and HUVECs ($7 \times 10^5$ cells) were placed in the upper chamber of the filter. The chamber was incubated at 37° C. for 18 h, and then the cells were fixed with 70% methanol and stained with hematoxylin and eosin. Invasiveness was measured by counting the number of whole cells on the lower side of the filter using a microscope at 100× magnification, and cells were photographed at 100× magnification [14].

Statistical Analysis

Results are expressed as the mean±standard error (SE). Student's t-test was used to determine the statistical significance between control and test groups. A p-value less than 0.05 was considered statistically significant.

Results and Discussion

Voacangine Potently Inhibits the Proliferation of HUVECs

Figure 1B:
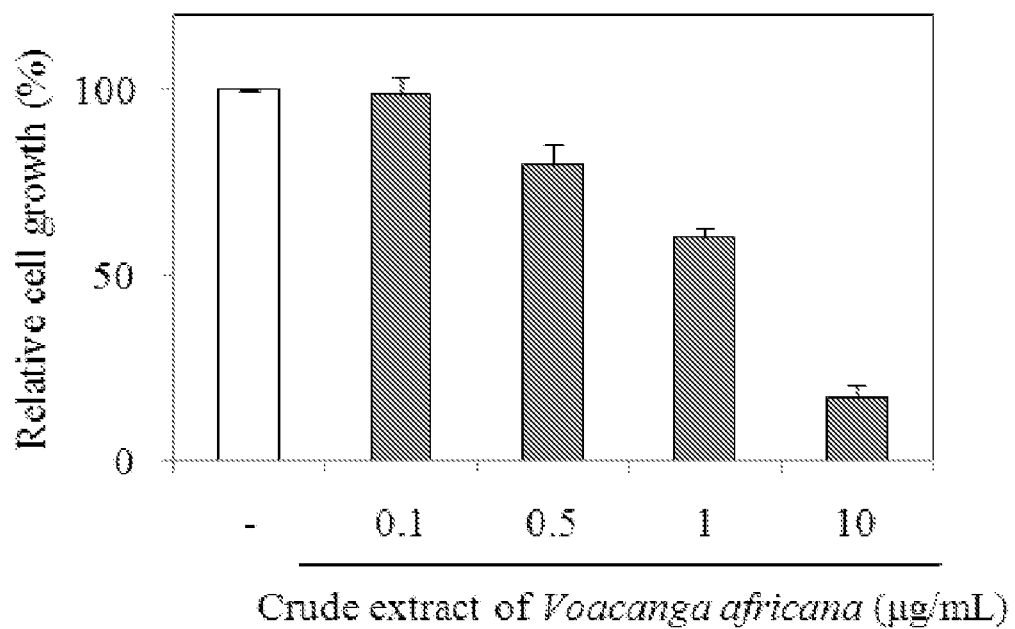
Figure 1C:
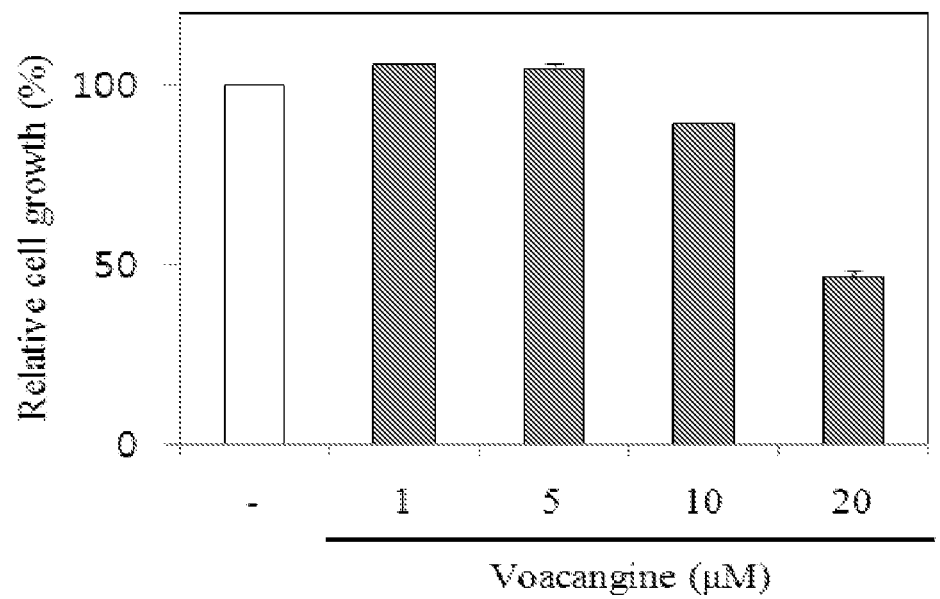

We found that the crude extract of *Voacanga africana* inhibits the proliferation of HUVECs in a dose-dependent manner (FIG. 1b). Voacangine is a known principal component of this extract. Therefore, we investigated whether voacangine is responsible for the observed anti-proliferative activity of the extract. As shown in FIG. 1C, voacangine inhibited cell growth at 10 μM. Notably, it exerted a greater growth inhibition effect on HUVECs than on other normal and cancer cell lines (Table 1).

TABLE 1

$IC_{50}$ values of voacangine on various cell lines

| | Normal cells | | Cancer cells | | |
|---|---|---|---|---|---|
| Cell lines | HUVECs | CHANG | HeLa | HT1080 | HepG2 |
| $IC_{50}$ (μM) | 18 | 26 | 23 | 33 | 42 |

Figure 1D:
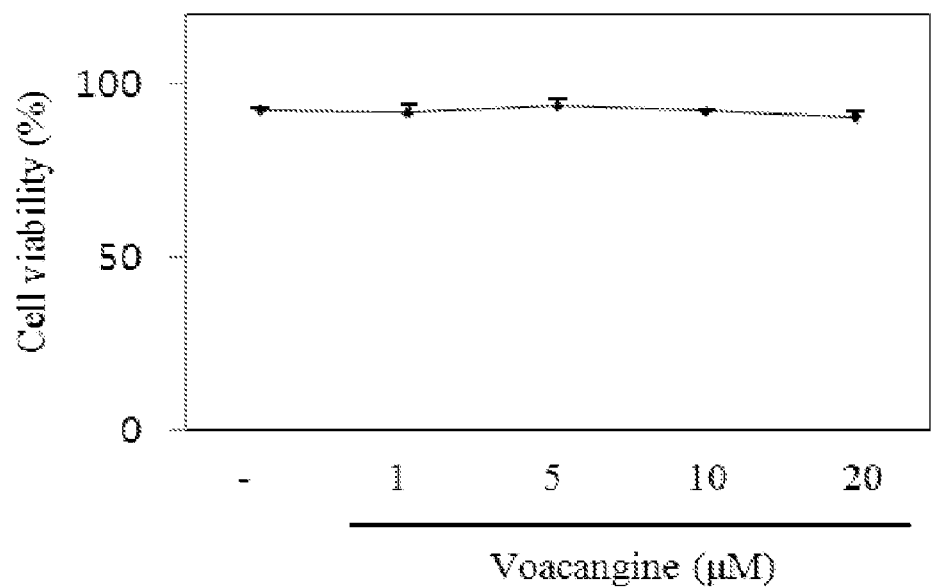

To determine the optimum dose of voacangine without cytotoxic side effects, various concentrations of voacangine (1-20 μM) were applied to HUVECs, and cell viability was determined using the trypan blue exclusion method. Voacangine exhibited no cytotoxicity on HUVECs at doses up to 20 μM for 3 days. Accordingly, the following studies were performed using a concentration range of 10-20 μM (FIG. 1d).

Voacangine Showed Anti-Angiogenic Activity In Vitro and In Vivo

Figure 2A:
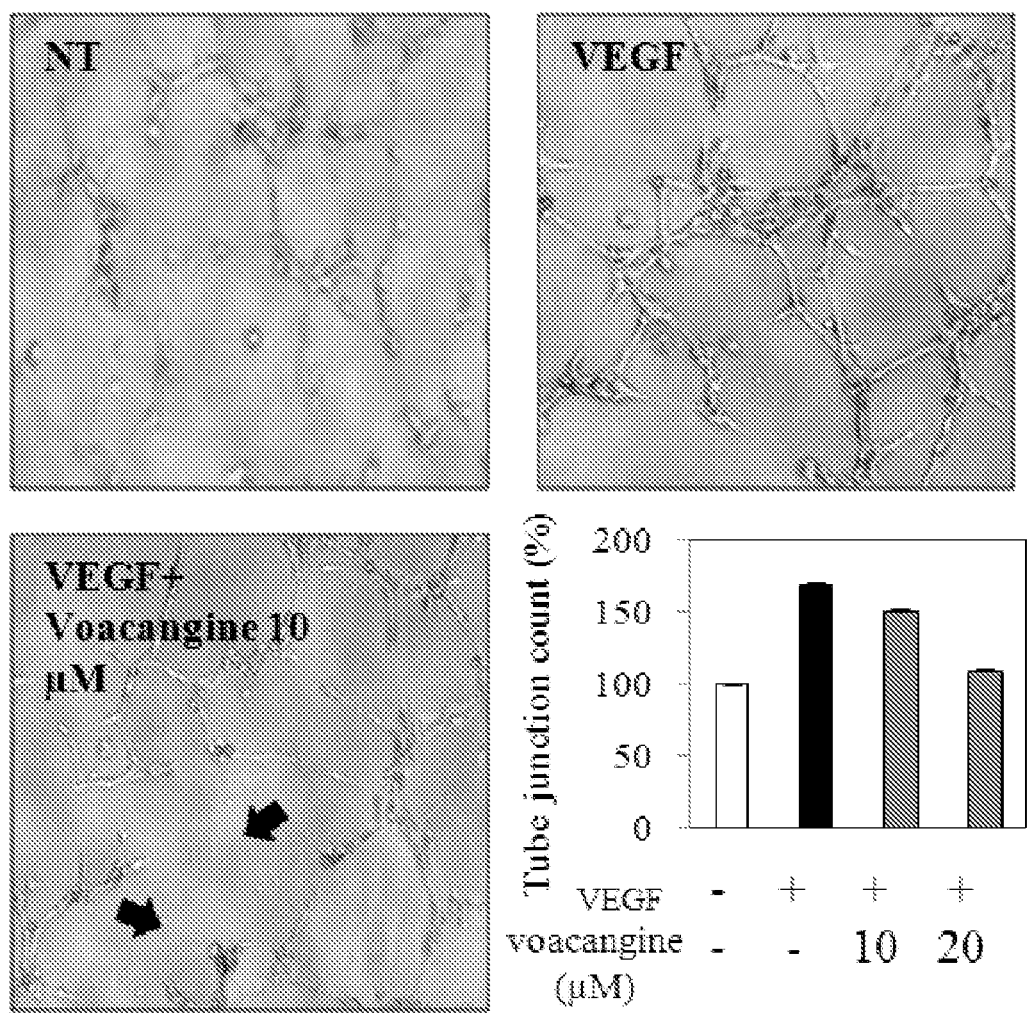
FIGS. 2a-2b represent anti-angiogenic activity of voacangine in vitro. Serum-starved HUVECs were stimulated by VEGF (30 ng/mL) in the presence or absence of voacangine.
Figure 2B:
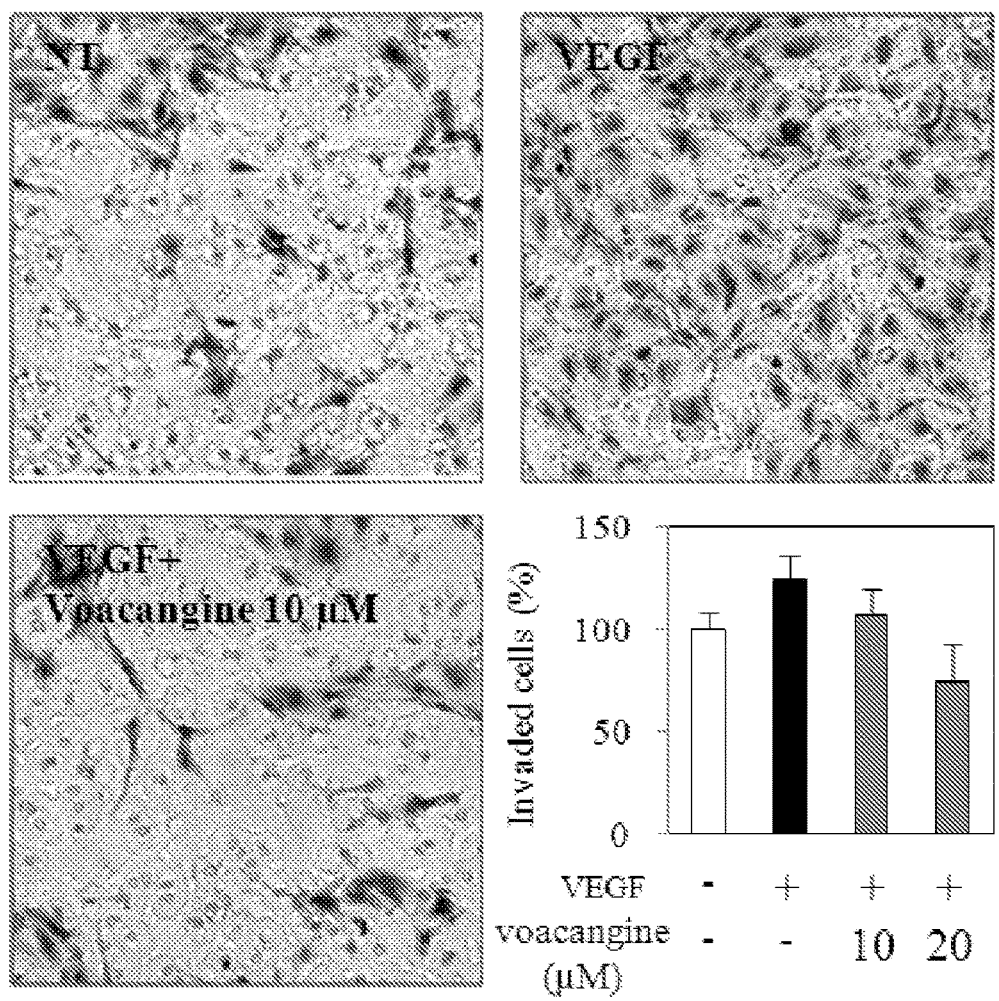

We next investigated the effect of voacangine on the angiogenic phenotypes of HUVECs in vitro, such as tube formation and chemoinvasion. Serum-starved HUVECs were stimulated by VEGF with or without voacangine. As shown FIG. 2a, voacangine inhibited VEGF-induced tube formation in a dose-dependent manner with no cytotoxic effects. The effect of voacangine on the invasive activity of HUVECs induced by VEGF was also investigated. Voacangine inhibited the VEGF-induced enhanced invasiveness of HUVECs in a dose-dependent manner (FIG. 2b). These data indicate that voacangine effectively inhibits VEGF-induced angiogenesis in vitro.

Figure 3:
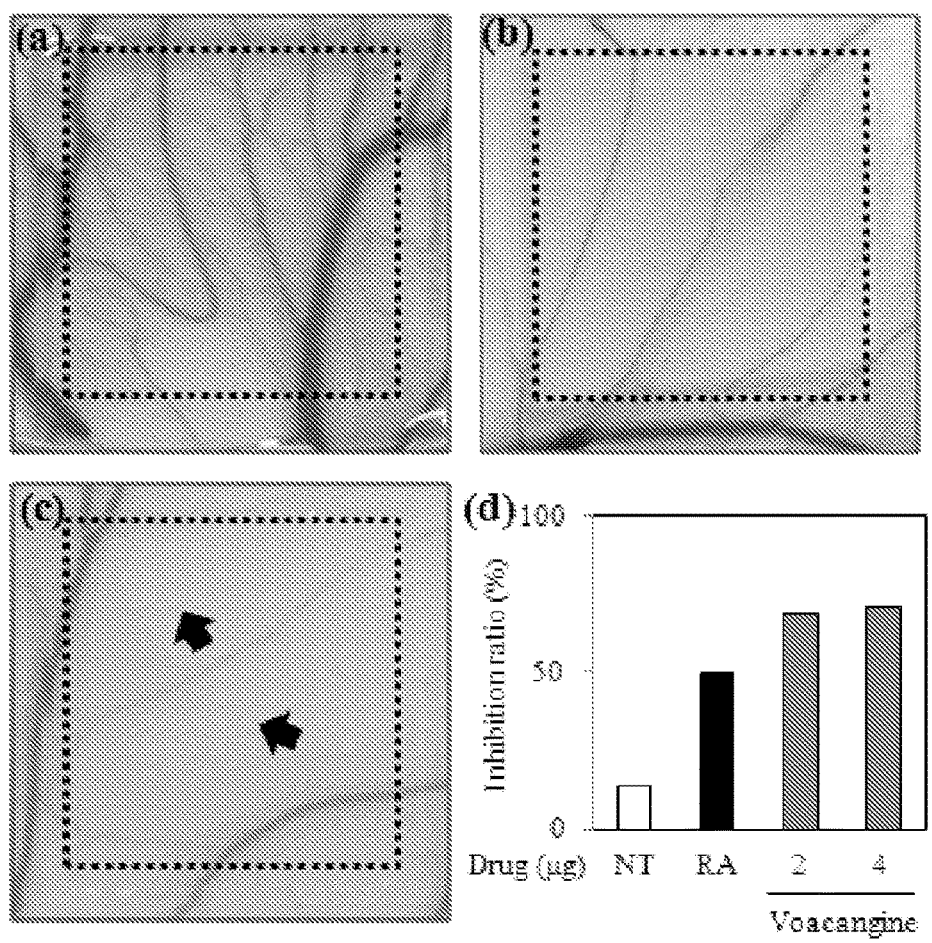
FIG. 3 represents anti-angiogenesis activity of voacangine in vivo. (a) EtOH control, (b) RA (1 μg/egg), (c) voacangine (2 μg/egg), and (d) voacangine (4 μg/egg) were applied to the CAM, and the membrane was observed. Arrows indicate inhibition of neovascularization of CAM by voacangine. Calculations were based on the proportion of positive eggs relative to the total number of eggs tested.

The anti-angiogenic activity of voacangine was further validated in vivo by using a chick embryo chorioallantoic membrane (CAM) assay. After treatment with voacangine for 2 days, the CAM was observed under a microscope. Normally, developed CAMs exhibit an extensive capillary network. However, voacangine dose-dependently inhibited capillary formation during CAM development with no apparent signs of thrombosis or hemorrhage (FIG. 3). These results demonstrate that voacangine potently inhibits angiogenesis both in vitro and in vivo without cytotoxic effects.

Voacangine Inhibits Tumor Cell-Induced Angiogenesis

Figure 4A:
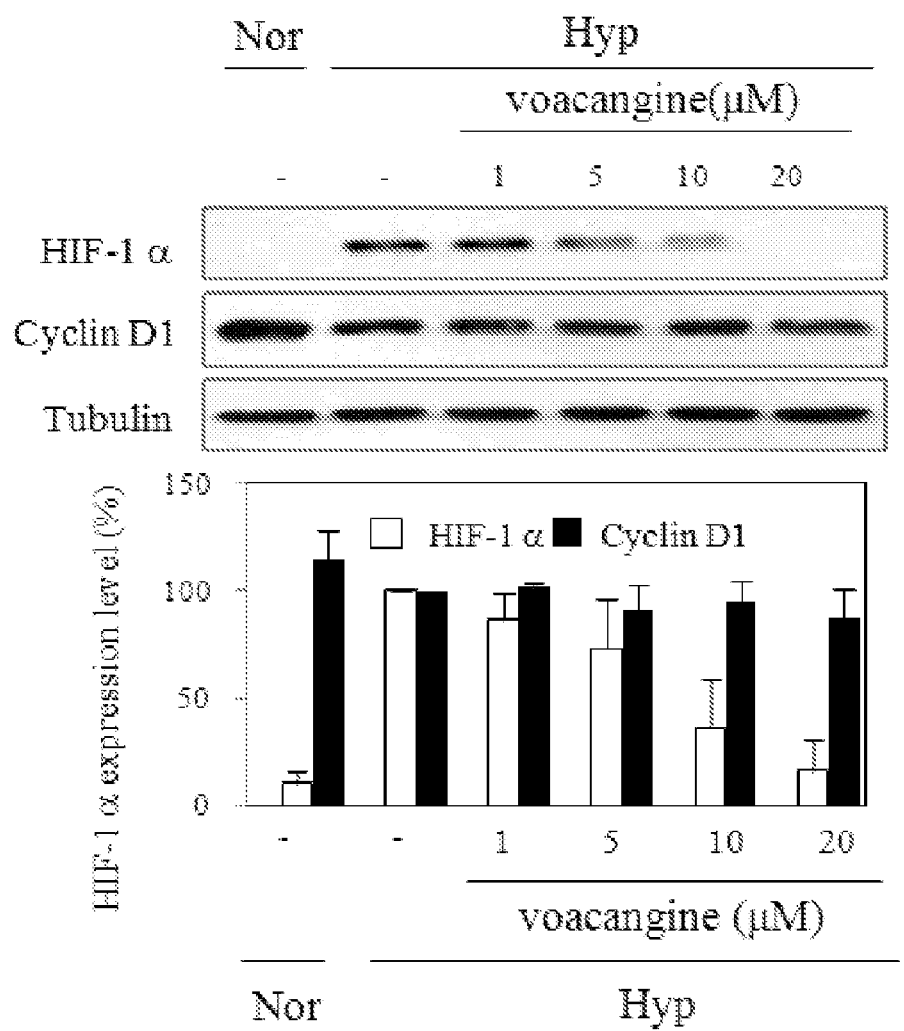
FIGS. 4a-4c represent the effect of voacangine on the expression of angiogenic factors.

Hypoxia-inducible factor-1α (HIF-1α) plays a key role in tumor angiogenesis by regulating the expression of angiogenic factors, including VEGF [15]. HIF-1α overexpression has been implicated in many human cancers. Thus, we examined the effect of voacangine on HIF-1α expression levels under hypoxic conditions. The expression level of HIF-1α in human hepatocellular carcinoma (HepG2) cells during hypoxia was dose-dependently reduced by voacangine without inhibiting the synthesis of other proteins related to the cell cycle (cyclin D1) and cytoskeleton (tubulin) (FIG. 4a).

Figure 4B:
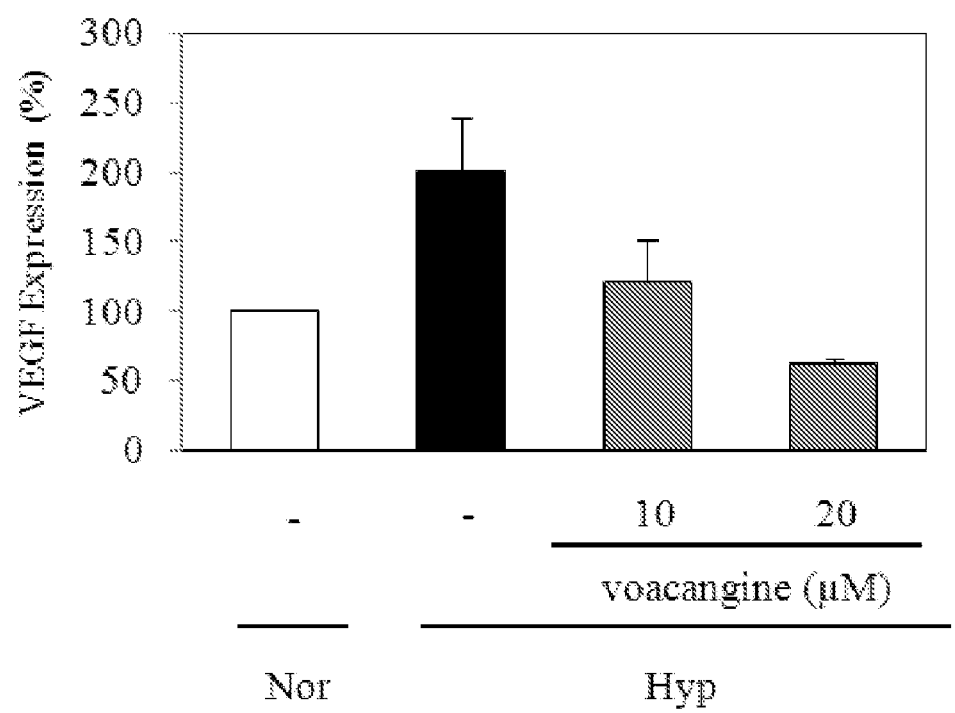
Figure 4C:
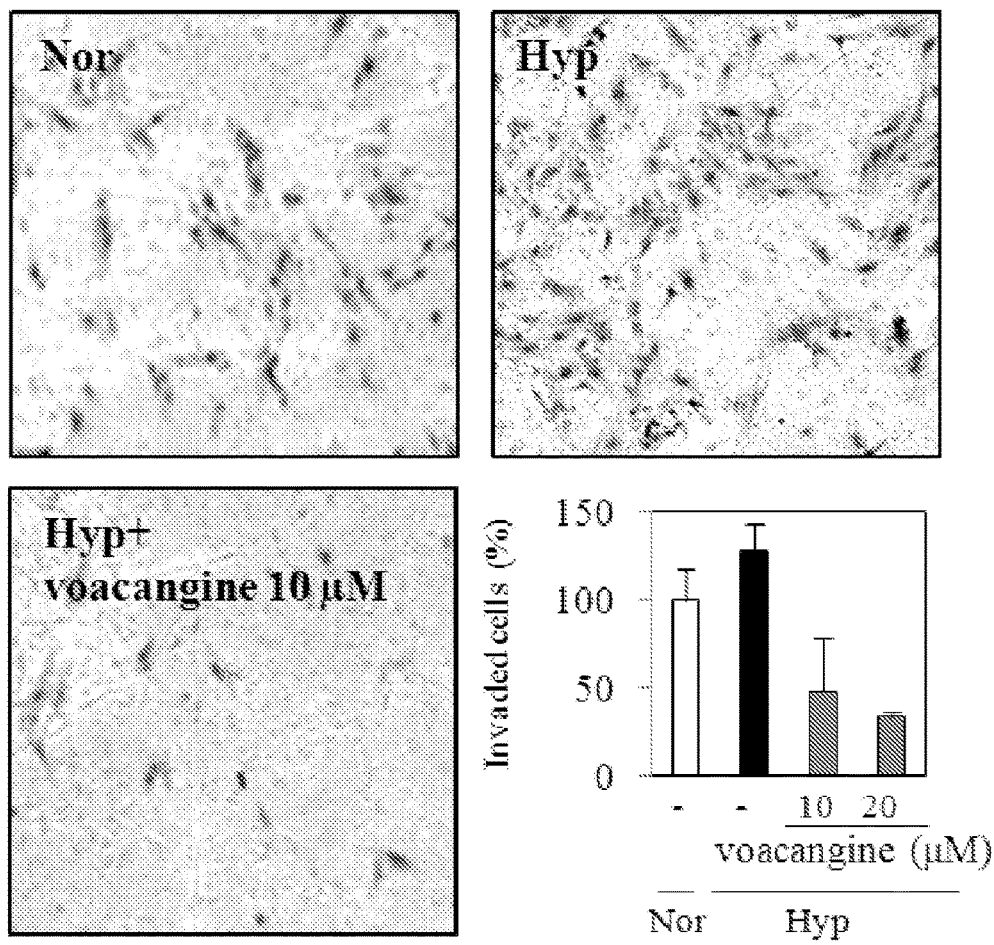
Figure 5A:
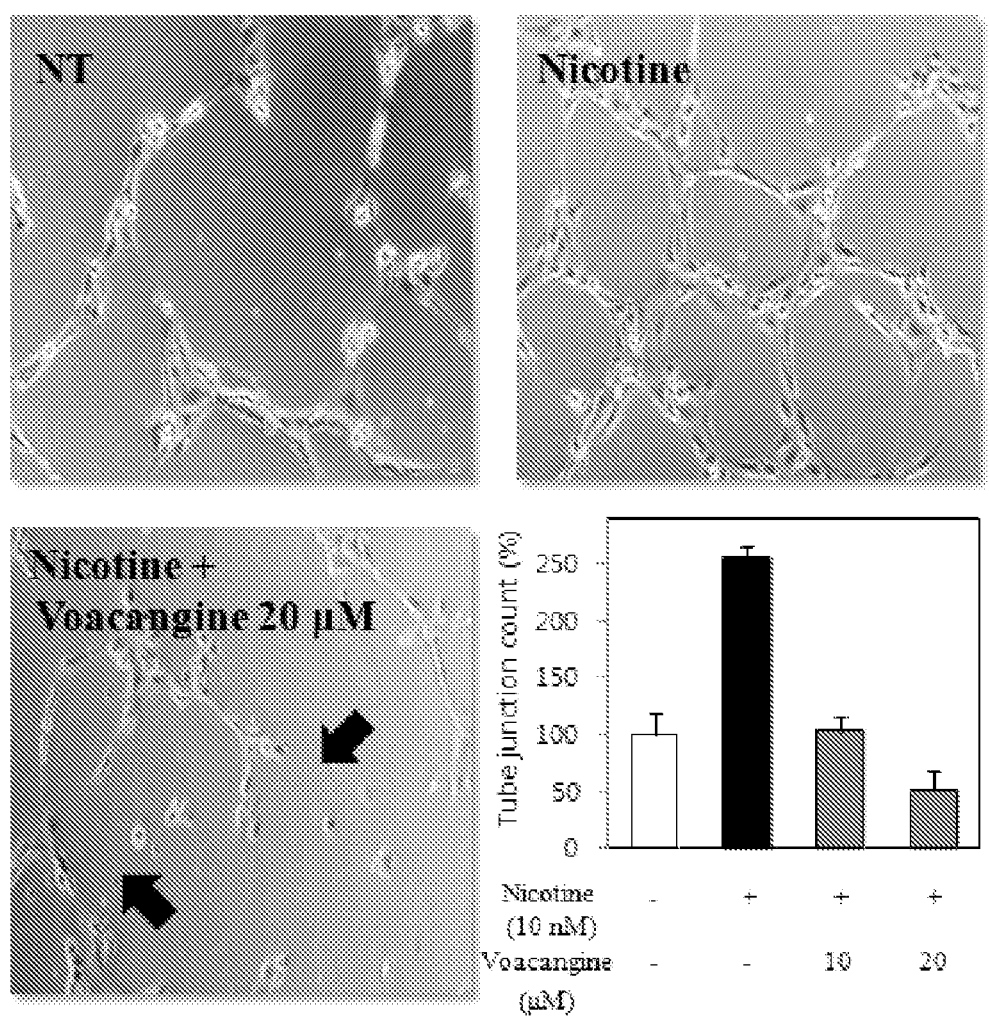
FIGS. 5a-5b represent the inhibitory effect of voacangine on nicotine-induced angiogenesis in vitro. Serum-starved HUVECs were stimulated by nicotine (10 nM) in the presence or absence of voacangine. The nicotine treatment was analyzed to increase angiogenesis and cell invasion activities by 2.5-fold and 2.0-fold, respectively, demonstrating that nicotine induces angiogenesis. Voacangine was revealed to inhibit nicotine-induced angiogenesis and invasion of HUVECs in a dose-dependent manner (FIGS. 5a and 5b).
Figure 5B:
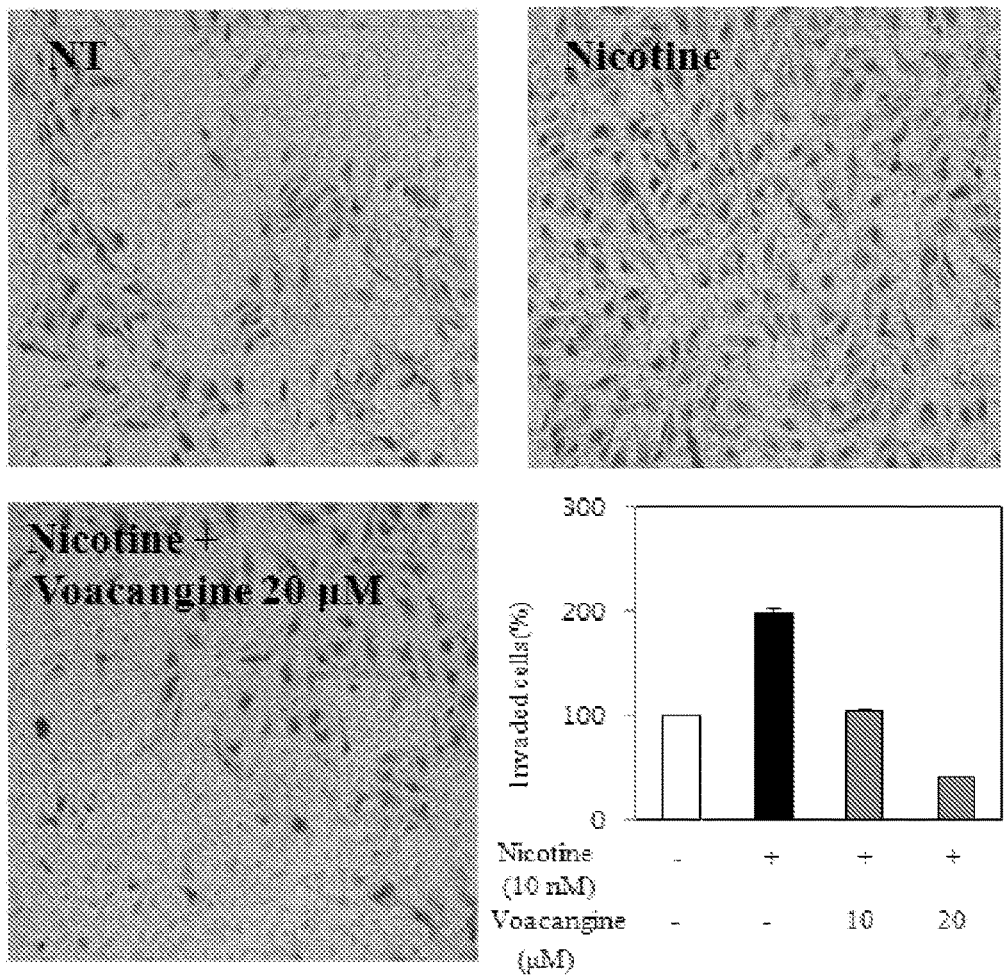

As the result of reduced HIF-1α expression, voacangine treatment inhibited the hypoxia-induced expression of VEGF, a HIF-1α target gene, in a dose-dependent manner (FIG. 4b). Moreover, tumor cell-induced invasiveness of HUVECs by hypoxia was dose-dependently inhibited by voacangine (FIG. 4c). These results demonstrate that voacangine potently inhibits tumor cell-induced angiogenesis through suppression of the angiogenic factor, HIF-1α, with no observed cytotoxic effects.

In this study, our results clearly demonstrate that voacangine, an active principal component of *Voacanga africana* extract, exhibits anti-angiogenic activity in vitro and in vivo. In HUVECs, the expression levels of HIF-1α and its target gene, VEGF, were dose-dependently suppressed by voacangine. In addition, voacangine inhibited tumor cell-induced invasiveness in a dose-dependent manner. Overall, these results suggest that this compound might provide the basis for the development of novel anti-angiogenic agents. It is noteworthy that voacangine effectively suppresses VEGF- and hypoxia-induced angiogenesis at lower doses than are necessary to inhibit HUVEC growth, suggesting that the compound may specifically perturb angiogenic signaling pathways. Moreover, the unique chemical structure of voacangine (with an iboga alkaloid as a core moiety) may provide new insights into the mechanisms underlying angiogenesis signaling pathways. Further investigation identifying and validating the targets of the small, naturally occurring molecule voacangine will help to decipher the interesting anti-angiogenic mechanisms of the compound and open a new gate into angiogenesis biology.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

[1] J. Folkman, Clinical applications of research on angiogenesis, N. Engl. J. Med. 235 (1995) 1757-1763.
[2] P. Carmeliet, Blood vessels and nerves: common signals, pathways and diseases, Nat. Rev. Genet. 4 (2003) 710-720.
[3] E. J. Battegay, Angiogenesis: mechanistic insights, neovascular diseases, and therapeutic prospects, J. Mol. Med. (Berl) 73 (1995) 333-346.
[4] D. Hanahan, J. Folkman, Patterns and emerging mechanisms of the angiogenic switch during tumorigenesis, Cell 86 (1996) 353-364.
[5] T. Andre, E. Chastre, L. Kotelevets, J. C. Vaillant, C. Louvet, J. Balosso, E. Le Gall, S. Prevot, C. Gespach, Tumoral angiogenesis: physiopathology, prognostic value and therapeutic perspectives, Rev. Med. Int. 19 (1998) 904-913.
[6] D. J. Newman, G. M. Cragg, Natural products as sources of new drugs over the last 25 years, J. Nat. Prod. 70 (2007) 461-477.
[7] M. Gordaliza, Natural products as leads to anticancer drugs, Clin. Transl. Oncol. 9 (2007) 767-776.
[8] C. G. Pereira, J. E. Carvalho, M. A. A. Meireles, Anticancer activity of *Tabernaemontana catharinensis* extract obtained by supercritical fluid extraction anticancer activity of extract of *Tabernaemontana catharinensis* obtained by supercritical extraction, Rev. Bras. Pl. Med., Botucatu, v. 8, n. 4 (2006) 144-149.
[9] M. W. Lo, K. Matsumoto, M. Iwai, K. Tashima, M. Kitajima, S. Horie, H. Takayama, Inhibitory effect of iboga-type indole alkaloids on capsaicin-induced contraction in isolated mouse rectum, J. Nat. Med. 65 (2011) 157-165.
[10] K. H. Kim, J. Y. Park, H. J. Jung, H. J. Kwon, Identification and biological activities of a new antiangiogenic small molecule that suppresses mitochondrial reactive oxygen species, Biochem. Biophys. Res. Commun. 404 (2011) 541-545.
[11] N. H. Kim, H. J. Jung, F. Shibasaki, H. J. Kwon, NBBA, a synthetic small molecule, inhibits TNF-alpha-induced angiogenesis by suppressing the NF-kappaB signaling pathway, Biochem. Biophys. Res. Commun. 391 (2010) 1500-1505.
[12] A. Albini, Y. Iwamoto, H. K. Kleinman, G. R. Martin, S. A. Aaronson, J. M. Kozlowski, R. N. McEwan, A rapid in vitro assay for quantitating the invasive potential of tumor cells, Cancer Res. 47 (1987) 3239-3245.
[13] H. J. Jung, J. S. Shim, H. B. Lee, C. J. Kim, T. Kuwano, M. Ono, H. J. Kwon, Embellistatin, a microtubule polymerization inhibitor, inhibits angiogenesis both in vitro and in vivo, Biochem. Biophys. Res. Commun. 353 (2007) 376-380.
[14] T. Garrido, H. H. Riese, M. Aracil, A. Perez-Aranda, Endothelial cell differentiation into capillary-like structures in response to tumour cell conditioned medium: a modified chemotaxis chamber assay, Br. J. Cancer 71 (1995) 770-775.
[15] C. Brahimi-Horn, J. Pouysségur, The role of the hypoxia-inducible factor in tumor metabolism growth and invasion, Bull Cancer 93(2006) 73-80.
[16] Heeschen C. et al, Nicotine stimulates angiogenesis and promotes tumor growth and atherosclerosis, Nat. Med. 7 (2001) 833-839

The invention claimed is:

1. A method for treating cancer selected from the group consisting of lung cancer, breast cancer, pancreatic cancer, thyroid cancer, and glioblastoma the method comprising administering to a subject in need thereof, a composition comprising as an active ingredient a compound represented by Chemical Formula 1 below:

Chemical Formula 1

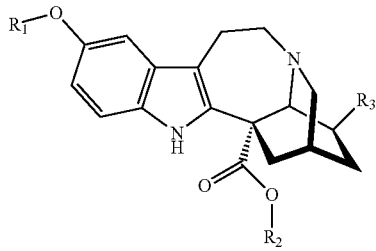

wherein, $R_1$, $R_2$, and $R_3$ each are independently hydrogen, $C_{1-12}$ alkyl, $C_{1-12}$ alkoxy, hydroxy, CN, $CONH_2$, halo, oxazolyl, $C_{1-12}$ alkylthio, or trifluoro($C_{1-2}$) alkyl.

2. The method of claim 1, wherein $R_1$, $R_2$, and $R_3$ each are independently hydrogen, halo, or $C_{1-12}$ alkyl.

3. The method of claim 1, wherein the compound is represented by Chemical Formula 2 below:

Chemical Formula 2

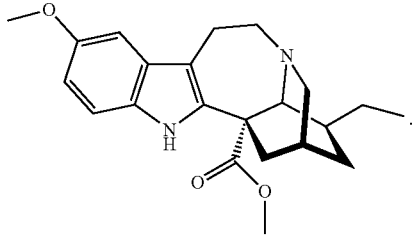

* * * * *